United States Patent [19]

Farrell et al.

[11] Patent Number: 5,265,483
[45] Date of Patent: Nov. 30, 1993

[54] SAMPLING VALVE

[75] Inventors: Michael D. Farrell, Brookfield; Eugene R. Rommelfaenger, Neosho, both of Wis.

[73] Assignee: Sentry Equipment Corp., Oconomowoc, Wis.

[21] Appl. No.: 980,991

[22] Filed: Nov. 24, 1992

[51] Int. Cl.⁵ .............................................. G01N 1/10
[52] U.S. Cl. ................. 73/863.86; 73/863.71; 73/863.73; 73/863.81; 422/103
[58] Field of Search ............ 73/863.71, 863.73, 863.81, 73/863.86; 422/103

[56] References Cited

U.S. PATENT DOCUMENTS

| | | | |
|---|---|---|---|
| 2,589,712 | 3/1952 | Langsenkamp et al. | 73/422 |
| 3,941,171 | 3/1976 | Ogle | 141/309 |
| 4,580,452 | 4/1986 | Masson | 73/863.86 |
| 4,651,574 | 3/1987 | Spencer | 73/863.86 |
| 4,662,231 | 5/1987 | Schaarschmidt et al. | 73/863 |
| 4,791,821 | 12/1988 | Spencer | 73/864.74 |
| 4,800,761 | 1/1989 | Spencer | 73/863.71 |
| 4,818,489 | 4/1989 | Conner et al. | 422/84 |
| 4,823,623 | 4/1989 | Carpenter et al. | 73/864.74 |
| 4,879,915 | 11/1989 | Spencer | 73/864.74 |
| 4,887,472 | 12/1989 | Jansen | 73/863.86 |
| 4,986,138 | 1/1991 | Spencer | 73/864.34 |
| 4,987,785 | 1/1991 | Spencer | 73/863.71 |
| 5,003,830 | 4/1991 | Spencer | 73/863.83 |
| 5,012,845 | 5/1991 | Averette | 141/329 |
| 5,116,330 | 5/1992 | Spencer | 73/863.71 |

OTHER PUBLICATIONS

Texas Sampling, Inc.—Product Brochure re "Announcing the New Liquid Sampler".

Primary Examiner—Timothy M. McMahon
Attorney, Agent, or Firm—Jansson & Shupe, Ltd.

[57] ABSTRACT

The improved sampling valve assembly includes a diverting valve and an optional isolation valve in series for providing redundant shutoff. The assembly includes rounded-end, side-ported needles (as part of an easily-replaced needle assembly) to pierce the receptacle septum without "coring" and help prevent liquid "carry-over." The assembly also has features providing metered, low pressure flow into the receptacle and very low dead volume. A receptacle guide has an interior cavity shaped like the receptacle to guide the inserted receptacle for aligned engagement of the septum with the needle assembly. The needle assembly is removable by removing only the keeper nut.

19 Claims, 7 Drawing Sheets

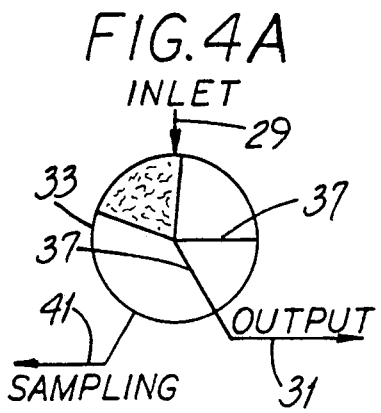
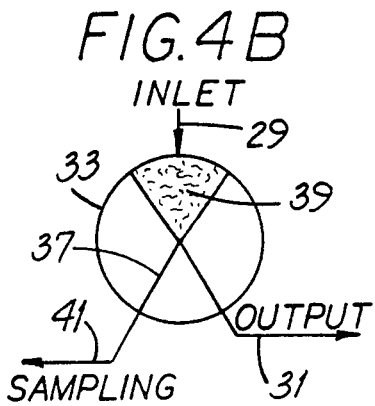
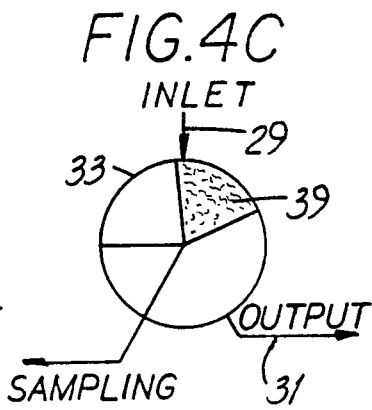
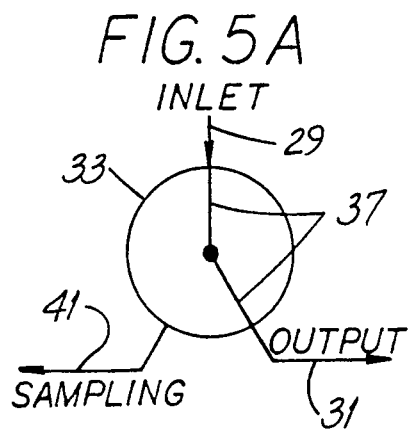
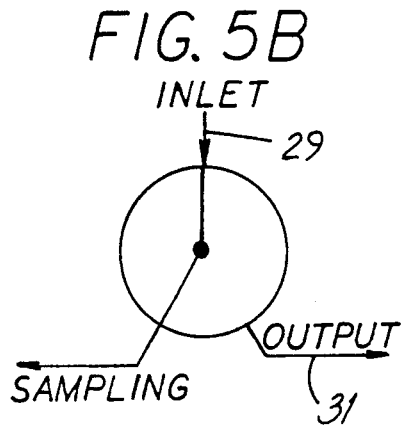
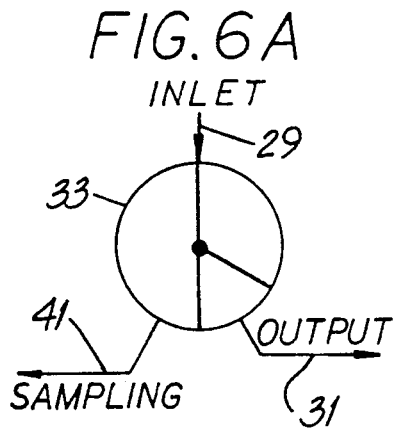
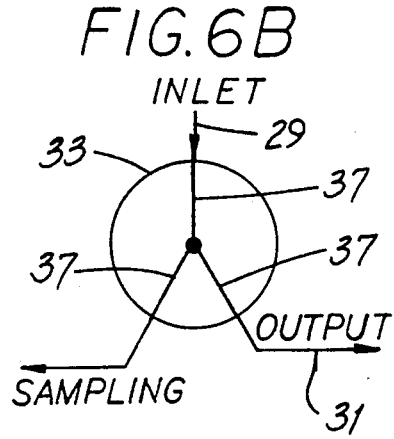

SAMPLING VALVE

FIELD OF THE INVENTION

This invention relates generally to fluid analysis and, more particularly, to analysis of samples of fluid drawn from process flow lines.

BACKGROUND OF THE INVENTION

The broad field of applied chemistry involves (among other things) manufacture of chemical compounds and use of such compounds in other manufacturing activity or in treatment of articles of manufacture. Such chemical compounds may include toxic and hazardous substances, petrochemical products and the like. And such compounds may be volatile.

During manufacture and use of such compounds, it is often required that some aspect of the compound be tested or analyzed periodically. Such testing or analysis may be to help maintain compound purity, to determine its concentration in a dilute mixture or merely to determine whether such compound is present in or absent from a particular process.

Earlier practice in this field involved providing a simple drain or sampling faucet in the wall of a vessel or in a flow line containing the compound. A sample was drawn into an open container and any residual compound which dripped from the faucet was permitted to fall to the earth or to the room floor.

Increasing concerns about maintaining the environmental quality of the earth and the air have largely eliminated such practices, at least where anything but an innocuous compound is involved. Such concerns have been evidenced by the proliferation of legislation directed to, among other things, sampling practices.

For example, in the United States, the 1990 amendments to the Clean Air Act of 1970 expanded the list of volatile organic compounds (VOCs) and hazardous air pollutants from seven to over one hundred eighty products. Such amendments also established leak standards for fugitive emissions for pumps, valve, compressors sampling connection systems and other devices and systems. As a result, the techniques for taking samples of, e.g., volatile organic compounds (VOCs) and the equipment used for doing so have been dramatically revised.

The following describes some aspects of known sampling-type devices. Among the features of such known devices are partial path purging, bevelled hypodermic-like needles apt to core the septum, single valve shutoff and the like. The patents mentioned below describe further specifics.

The machine-like injector shown in U.S. Pat. No. 5,012,845 (Averette) uses a needle having dual concentric passages. After injection is complete, the needle is drawn upward into a valve block until its lower side port is in registry with a source of purging gas. Needle purging is "upstream," i.e., the purging gas and any liquid advanced by it is forced into the transparent barrel. The outer annular passage is apparently not purged at all.

The device shown in U.S. Pat. No. 4,580,452 (Masson) has a type of ball valve and a truncated valving stem seated in a cone-shaped aperture in the side wall of a liquid process line. Other hardware, with or without an additional shutoff valve, is connected to the side wall when a sample is to be drawn. The advantages are said to be that the device has no "dead volume" and a sample can be drawn without leakage to the environment. The patent describes purging before taking a sample and observes that the invention eliminates the need for such purging.

U.S. Pat. No. 4,823,623 (Carpenter et al.) describes a transfer device having a two-way valve, a pair of needles of different lengths and spaced guide rods which guide a vial into position. Trade literature of Tech-Quip, Inc. (a/k/a Texas Sampling Inc.) depicts a liquid sampler having a single two-way ball valve rotatable to "through-flow" or sampling positions but not both simultaneously. The sampling needles are hypodermic-like and the protective bottle shroud has an internal sleeve and an axial sight groove. Trade literature of Dopak Inc. illustrates other types of sampling devices.

Needles shown in the Carpenter et al. patent and Tech-Quip, Inc. literature are sharply pointed, bevelled and have downward-opening passages. Such needles are precisely the shape most likely to "core" the receptacle septum as it is being pierced by the needles.

And some of the prior art devices are understood to retain a significant "dead volume" of liquid after the liquid sample is taken. Such dead volume can drip and contaminate the surroundings or undesirably evaporate into the atmosphere.

An improved sampling valve assembly which offers redundant shutoff, low pressure sampling, optional "full-passage" purging, substantial avoidance of septum coring and minimum "dead volume" would be an important advance in the art.

OBJECTS OF THE INVENTION

It is an object of the invention to provide an improved sampling valve overcoming some of the problems and shortcomings of the prior art.

Another object of the invention to provide an improved sampling valve having an optional redundant shutoff feature.

Another object of the invention to provide an improved sampling valve permitting supplying a sample to a receptacle while yet avoiding interruption of process line flow of the product being sampled.

Still another object of the invention to provide an improved sampling valve permitting metered, low-pressure fluid flow to the receptacle.

Yet another object of the invention to provide an improved sampling valve having an optional "full-purge" feature.

Another object of the invention to provide an improved sampling valve configured to help avoid frothing of the liquid being sampled and to help avoid receptacle blowoff.

Another object of the invention to provide an improved sampling valve having an easily-replaced needle assembly configured to substantially avoid "coring" the receptacle septum pierced by the needles.

Another object of the invention to provide an improved sampling valve having a needle assembly configured to help avoid fluid "carryover" between needles.

Still another object of the invention to provide an improved sampling valve having a minimum entrapped dead volume. How these and other objects are accomplished will become more apparent from the following descriptions taken in conjunction with the drawing.

SUMMARY OF THE INVENTION

The invention facilitates drawing a specimen sample of a volatile organic compound (VOC) or other volatile or toxic fluid, usually a liquid, from a flow line containing the fluid. In general, sampling valves have one or two needles which pierce a receptacle-sealing septum and flow the fluid into the removable receptacle for later laboratory analysis. The invention is an improvement in a sampling-type valve assembly having an input flow line, an output flow line and a diverting valve. The diverting valve has an inlet port receiving fluid from the input flow line and a sampling port directing the fluid to a receptacle in which the specimen is received.

The improvement comprises an optional isolation valve between the sampling port and the receptacle for providing redundant shutoff. That is, either the diverting valve or the isolation valve (or both) will close the flow passage extending from the diverting valve to the receptacle. The diverting valve includes an output port in flow communication with the sampling port and permitting fluid flow from the input flow line to the sampling port and the output port.

In a highly preferred arrangement, the isolation valve is in series with the diverting valve and the receptacle and has a valving member mounted for movement in a continuum between a fully closed position and a fully open position. So configured, the isolation valve can be "cracked" open a small amount (or "metered" open, as sometimes referred to), thereby permitting metered fluid flow to the receptacle.

The three-way diverting valve, preferably having a ball-type valving member, can have any of plural arrangements. In one highly preferred exemplary arrangement, the valving member is mounted for movement in a continuum between a first position, an intermediate position and a second position. In the first position, the valving member connects the inlet port only to the output flow line. In the intermediate position, such member connects the inlet port to the output flow line and to the isolation valve while the second position, it connects the inlet port only to the isolation valve.

In another exemplary arrangement, the valving member is mounted for movement between a first position connecting the inlet port to the output flow line and a second position connecting the inlet port to the isolation valve. So arranged, fluid flow is to the output flow line or to the isolation valve alternatively.

In yet another exemplary arrangement, somewhat like that described immediately above, the second position of the valving member connects the inlet port to both the output flow line and the isolation valve simultaneously. Of course, limits of valve handle travel may be set by adjustable stops.

In the first and third exemplary arrangements described above (and when the diverting valve is properly positioned), such valve permits taking the sample without stopping normal flow between the input flow line and the output port. The sample thus taken is more representative of the fluid flowing in the line than would be the case if such line were shut off during sampling.

Furthermore, such first and third exemplary arrangements may result in a significant pressure drop across the diverting valve as the sample is being taken. In process flow lines at elevated pressure, such pressure drop can be a distinct advantage when taking a sample. More information regarding the undesirability of taking a sample at elevated pressure and regarding the solution offered by the unique valve assembly is set out below.

The sampling port of the diverting valve includes a port exit, i.e., that portion of the sampling port immediately adjacent to the stationary valve block in which the valving member moves. The valve assembly also includes a vent port and in another aspect of the invention, there is a fluid flow passage extending from the port exit to the vent port.

An optional purge passage is in flow communication between a source of purging gas, e.g., pressurized nitrogen, and the port exit for purging the fluid flow passage of vagrant fluid which may be lodged therein. Substantially all such fluid may be purged from the assembly through the vent port to a charcoal canister or the like. Such fluid is thus prevented from evaporating into the atmosphere or dripping to the ground.

Process flow lines from which specimen samples are to be taken may be at significant pressure and a pressure of a few hundred pounds per square inch would not be uncommon. The new valve assembly has features in recognition of this possibility and of the desirability (for several reasons) of taking a sample at relatively low pressure.

Accordingly, the assembly has a needle flowing fluid from the sampling valve to the receptacle. In a highly preferred embodiment, such assembly also includes a pressure reducing orifice between the needle and the diverting valve and, more specifically, between the diverting valve and the isolation valve and adjacent to the port exit of the sampling valve. An advantage of such orifice is that if the user opens the diverting valve wide open to the isolation valve and also manipulates the isolation valve to its full open position (i.e., without "cracking" either valve), reduced-pressure fluid sampling is nevertheless provided.

So-called low pressure sampling is desirable for several reasons. It aids in more deliberate filling of the receptacle at a lower fill rate so that the volume of the drawn sample can be more closely controlled. In valve assemblies lacking the unique needle assembly described below, it also helps prevent receptacle "blow-off" as might occur which the high pressure fluid stream impinges on the bottom of the receptacle. And low pressure sampling also helps prevent carryover of fluid from the receptacle to the vent port.

In another aspect, the inventive assembly includes a nozzle in flow communication with the sampling valve and the receptacle. A needle assembly is attached to the nozzle, is detachable as a unitary assembly and has a sampling needle and a venting needle. For reasons mentioned in the detailed description, it is preferred that such needles be of different lengths. In the invention, at least one needle (and preferably each needle) has a rounded or blunt end whereby septum coring is substantially prevented. This feature is better appreciated when contrasted with conventional "hypodermic-like" needles having a sharp-edged tip and an angled face which often cut a neat, disc-like core out of the septum. Volatile fluids thereby undesirably escape from the receptacle.

And that is not all. In another aspect of the invention, the sampling needle includes a long axis extending toward the bottom of the bottle-like receptacle. A fill port (the small opening from which a liquid flows from the needle into the receptacle) extends along a port axis generally normal to the long axis of the needle. This "side-porting" arrangement substantially avoids liquid frothing. And when the fill port is directed away from the user, it helps prevent spraying the user with liquid in the event of receptacle breakage or user error.

In a highly preferred embodiment, the venting needle includes a vent port and the fill port and the vent port are directed generally away from one another. This helps avoid fluid "carryover" which may occur if fluid expelled from the fill port is directed toward the vent port of the venting needle.

More specifically, the sampling needle and the venting needle each include a long axis extending toward the receptacle bottom. The fill port is along an axis generally normal to the long axis of the sampling needle, the vent port is along an axis generally normal to the long axis of the venting needle and the fill port and the vent port are directed generally away from one another for avoiding fluid carryover.

And there are yet other features which help make the new valve assembly very convenient to use. The assembly has a lower end and a generally cylindrical receptacle guide attached thereto. The receptacle guide has an interior cavity generally conforming to the shape of the receptacle and, more specifically, such cavity has a first substantially cylindrical portion and a second tapered portion. The tapered portion helps guide the receptacle cap to the axial center of the guide as the receptacle is inserted into the guide.

When the receptacle is inserted into the guide preparatory to taking a sample, the receptacle is guided for aligned engagement of the septum with the needle assembly and when fully inserted into the guide, the receptacle cap "stops" against the needle assembly keeper nut described below. Such arrangement helps assure that the septum is normal to the long axes of the needles and that receptacle movement is along such axes. The potential for damage to the needles and/or for septum tearing is thereby reduced. The receptacle guide (which is preferably of one-piece construction) also includes an elongate viewing aperture permitting visual inspection of the receptacle contents and, more particularly, of the level of fluid in the receptacle.

The configuration of the guide and its relationship to the other parts of the assembly offers several advantages. Specifically, such configuration and relationship aid in (a) avoiding septum damage arising from misaligned receptacle insertion, (b) avoiding needle damage from the same cause, (c) protecting exposed needles from "knock and bump" damage, (d) shielding the user in event of spillage or breakage, (e) easily viewing the progress of filling, and (f) protecting the user from contact with the needles.

Another innovative feature of the valve assembly relates to the fact that the needle assembly is retained by a keeper nut limiting travel of the receptacle to a location where the needles have pierced the septum. The needle assembly is removable by removing the keeper nut while yet avoiding disassembly of the valve assembly or disconnecting a line therefrom.

Other details of the inventive valve assembly are set forth in the following detailed description and in the drawing.

BRIEF DESCRIPTION OF THE DRAWING

FIGS. 4A–4C are symbolic views of differing positions of one embodiment of the diverting valve component of the assembly of FIG. 1.

FIGS. 5A–5B are symbolic views of differing positions of another embodiment of the diverting valve component of the assembly of FIG. 1.

FIGS. 6A–6B are symbolic views of differing positions of yet another embodiment of the diverting valve component of the assembly of FIG. 1.

DETAILED DESCRIPTION OF PREFERRED EMBODIMENTS

The new sampling valve assembly 10 responds to a need to obtain samples of a fluid, typically a liquid rather than a gas, containing or possibly containing VOCs, toxic or hazardous substances or the like. At the same time, such assembly 10 offers features helping to conform such activity to applicable law.

Figure 1:
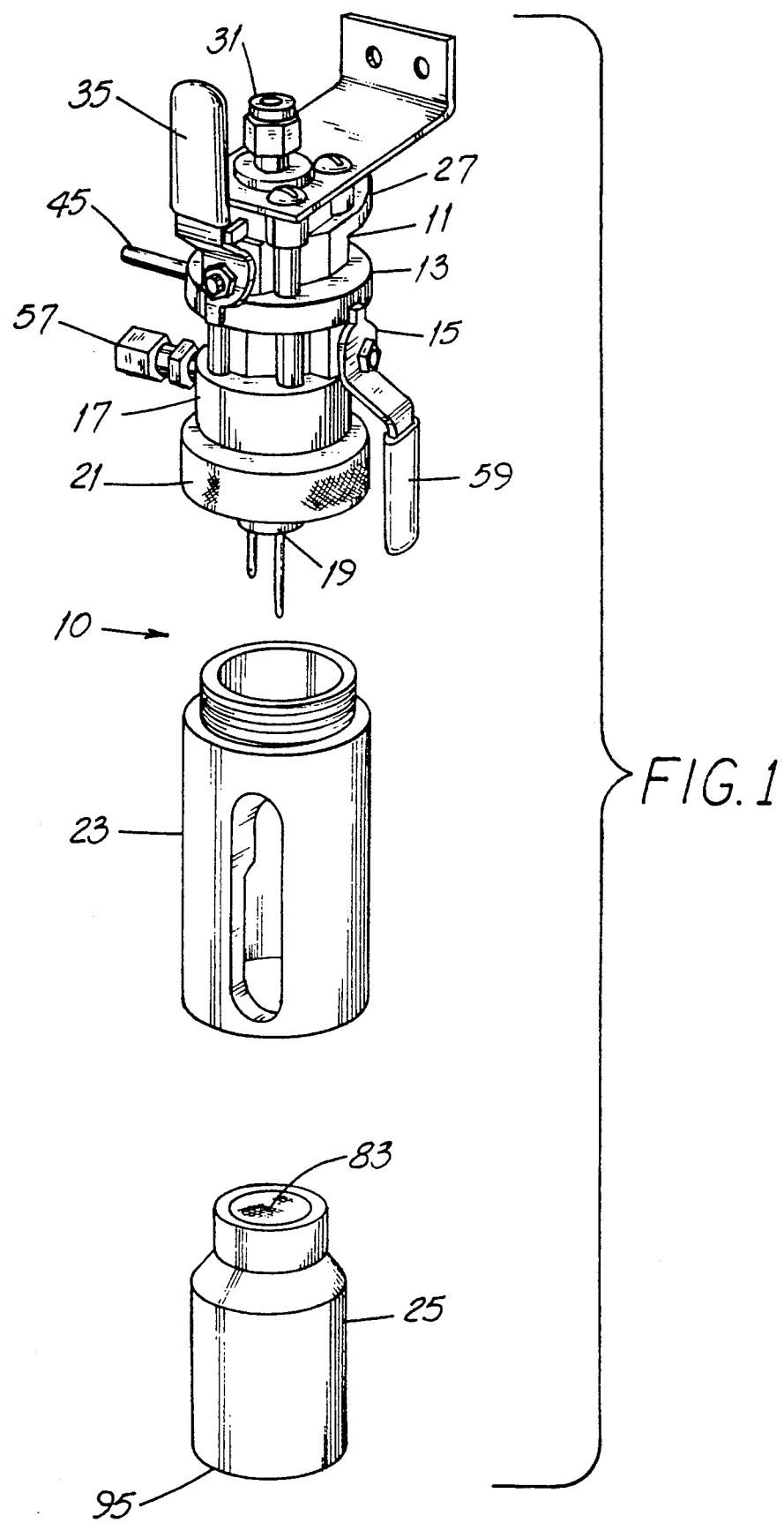
FIG. 1 is a perspective view of the improved sampling valve assembly shown in connection with a septum-closed receptacle used therewith.
Figure 2:
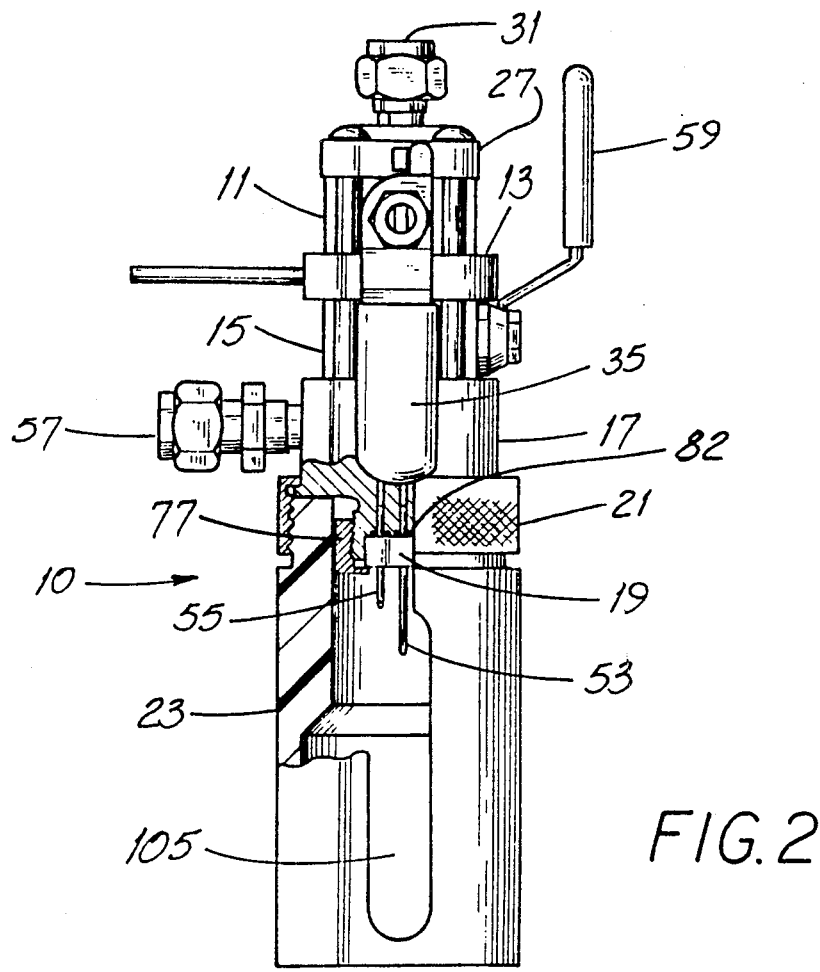
FIG. 2 is an elevation view of the assembly of FIG. 1 with parts shown in cross section.

Referring to FIGS. 1 and 2, the new sampling valve assembly 10 includes, in order from top to bottom, a diverting valve 11, an orifice plate 13, an isolation valve 15, a needle/vent housing 17, a needle assembly 19, a receptacle guide attachment ring 21 and a receptacle guide 23. The valves 11, 15 are preferably of the rotatable ball type and such valves 11,15 per se are made by Whitey Co. of Highland Heights, Ohio, and others. FIG. 1 also illustrates the receptacle 25 into which the sample is taken.

Figure 3:
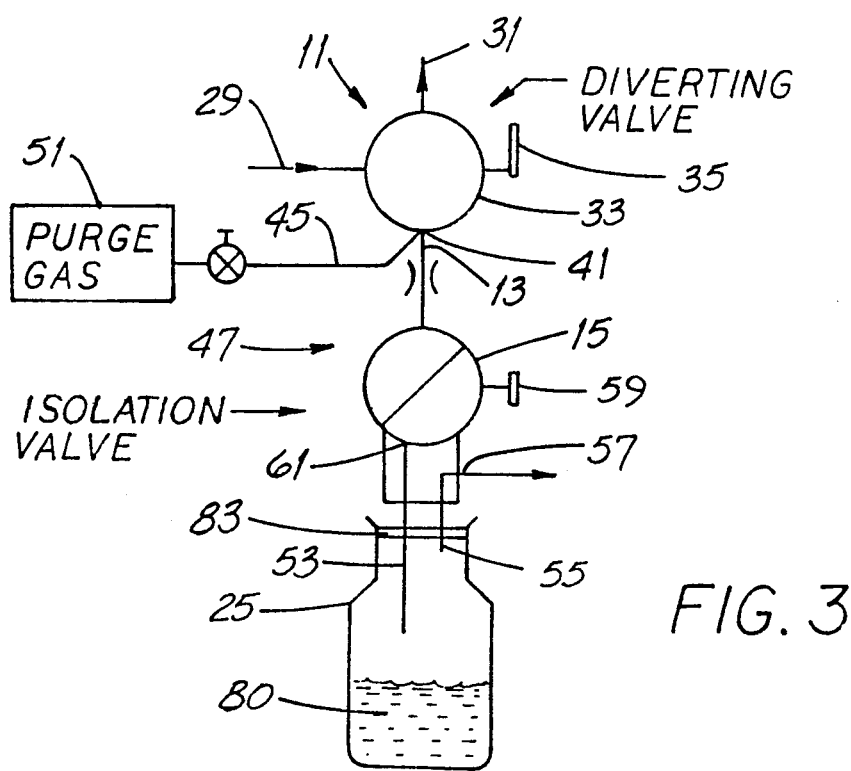
FIG. 3 is a representative schematic view of one embodiment of the valve assembly of FIG. 1 with the receptacle guide.

Referring also to FIG. 3, the diverting valve 11 has a valve body 27 to which are connected a side-mounted input flow line 29 and a top-mounted output flow line 31, such lines 29, 31 carrying the product to be periodically sampled. A valving member 33 is mounted in the body 27 and is attached to an operating handle 35 for rotating movement. In FIG. 3, the passage arrangement of such valving member 33 has been left blank since a number of such arrangements are possible and a few are shown in FIGS. 4, 5 and 6.

FIG. 4 shows a valving member 33 mounted for movement in a continuum between a first position, shown in FIG. 4A, an intermediate position, shown in FIG. 4B, and a second position shown in FIG. 4C. In the first position, the valving member 33 connects the inlet line 29 only to the output flow line 31. In the intermediate position, the valving member 33 connects the inlet line 29 to the output flow line 31 and to the isolation valve 15 and in the second position, the valving member 33 connects the inlet line 29 only to the isolation valve 15.

In the arrangement of FIG. 4B, the intermediate position permits the input flow line 29 to be connected to the output flow line 31 and to the isolation valve 15 simultaneously.

In the arrangement of FIG. 5, the valving member 33 is mounted for movement between a first position, FIG. 5A, connecting the inlet line 29 to only the output flow line 31 and a second position, FIG. 5B, connecting the inlet line 29 to only the isolation valve 15. In this arrangement, fluid flow is to the output flow line 31 or to the sampling valve 15, alternatively.

FIG. 6 shows a valving member 33 mounted for movement between a first, closed position, FIG. 6A, and a second, open position, FIG. 6B. In the first position, the inlet line 29 connects to neither the output flow line 31 nor to the isolation valve 15. In the second position, the inlet line 29 connects to both.

Certainly, those of ordinary skill will appreciate that the straight lines in FIGS. 4, 5 and 6 represent flow passages 37 having some nominal cross-sectional area. It will also be appreciated that the darkened areas 39 in FIGS. 4A, 4B and 4C represent an enlarged opening which remains in flow communication with the inlet line 29 irrespective of the position of the valving member 33. And the separate passages 37 leading to the output flow line 31 and to the isolation valve 15 in FIG. 4B can be replaced by a single passage embodied as an opening sufficiently large to span both the output flow line 31 and the isolation valve line 41.

In the first and third exemplary arrangements described above (and when the diverting valve 11 is properly positioned), such valve 11 permits taking the sample without stopping normal flow between the input flow line 29 and the output flow line 31. The sample thus taken is more representative of the fluid flowing in the line 31 than would be the case if such line 31 were shut off during sampling.

Furthermore, such first and third exemplary arrangements can provide a significant pressure drop across the diverting valve 11 as the sample is being taken. In process flow lines 29, 31 at elevated pressure, such pressure drop can be a distinct advantage when taking a sample. The underlying reasons are explained below.

Figure 7:
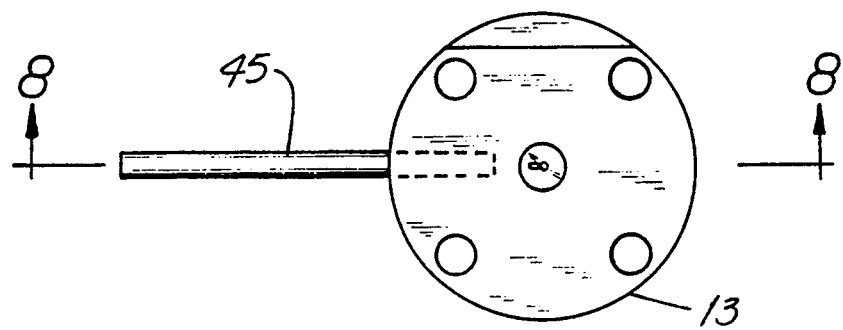
FIG. 7 is a top plan view of the orifice plate component of the assembly of FIG. 1 and showing the optional purge passage. Parts are shown in dashed outline.
Figure 8:
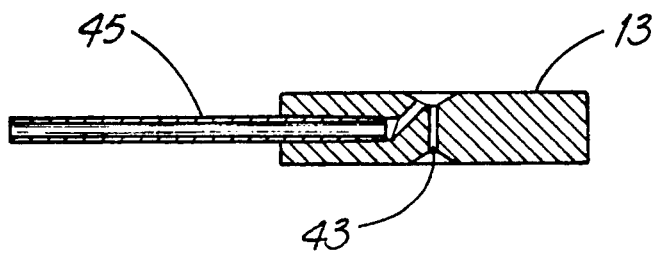
FIG. 8 is a cross section view of the orifice plate of FIG. 7 taken along the viewing plane 8—8 thereof.
Figure 9:
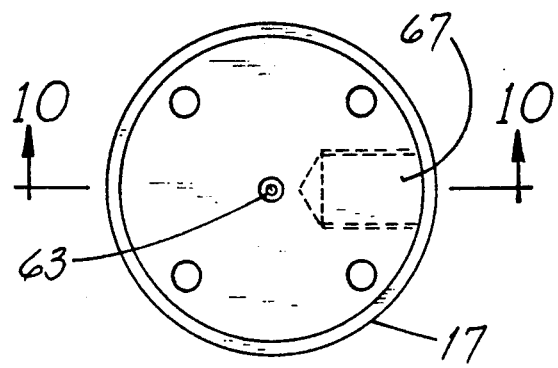
FIG. 9 is a top plan view, with part in dashed outline, of the needle/vent housing component of the assembly of FIG. 1.
Figure 10:
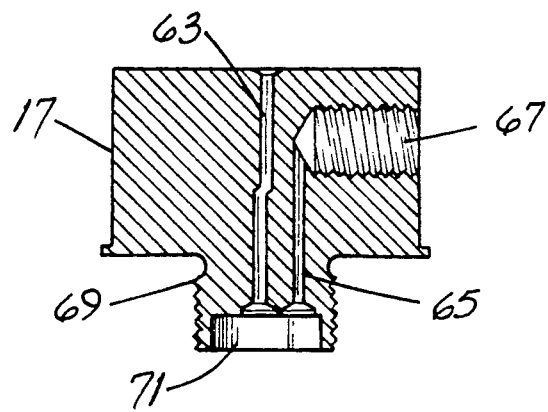
FIG. 10 is a cross section view of the needle/vent housing of FIG. 9 taken along the viewing plane 10—10 thereof.

Referring also to FIGS. 7 and 8, a disc-like, pressure-reducing orifice plate 13 is interposed between the diverting valve 11 and the isolation valve 15 to help assure that samples can be drawn at relatively low pressure, notwithstanding an elevated process line pressure. The plate 13 includes an orifice passage 43 of suitably small diameter. The passage 43 restricts flow and in the event of elevated process line pressure, creates a substantial pressure drop so that the pressure at the isolation valve 15 is reduced, perhaps dramatically reduced. Such small passage 43 also helps reduce the dead volume contained in the assembly 10.

As an optional feature, the new assembly 10 also includes a purge passage 45 for removing even the small amount of residual "dead volume" liquid from the flow passage 47. Viewing FIG. 3, it is to be appreciated that the diverting valve 11 has a sampling line 41, i.e., an opening in the valve body 27 leading to the orifice plate 13. The passage 45 is in flow communication between a source of purging gas 51, e.g., pressurized nitrogen, and (in the highly preferred embodiment) the sampling line 41.

That is to say, the purge passage 45 is arranged to remove substantially all of the liquid from within the assembly 10 except, perhaps, for a very small amount trapped in the diverting valve 11. Briefly described, it does so by flowing purging gas through the orifice plate 13 at that area of the plate 13 in contact with the ball valve of the diverting valve 11. Purging gas also flows through the isolation valve 15, the sampling needle 53 and the venting needle 55. The latter is connected to a vent connection 57 extending to a vapor-collecting device (e.g., a carbon canister or the like—not shown) of a known type. In other words, no vagrant liquid is left to drip on the ground or evaporate into the air when the sample receptacle 25 is not in place.

As illustrated in FIG. 3, a preferred isolation valve 15 is of the two-way, ball type. Rotation of the ball (by turning the handle 59) connects the orifice plate 13 to the needle/vent housing 17.

Referring also to FIGS. 9-12, the lower or "downstream" end 61 of the isolation valve 15 is terminated by a generally cylindrical needle/vent housing 17 having an axial passage 63 leading to a sampling needle 53. Such housing 17 also has a passage 65 spaced radially from the passage 63, leading to a venting needle 55 and connecting to a threaded, radial vent opening 67. The passage 65 and the vent opening 67 connect the venting needle 55 to the vent connection 57 and thence to a canister as described above.

The housing 17 includes a necked-down, tube-like nozzle 69 which includes an exterior thread and a pocket 71 for receiving the needle assembly 19 described below. When the needle assembly 19 is seated in the pocket 71, the upward extending ferrules of the sampling needle 53 and the venting needle 55, ferrules 73 and 75, respectively, are in sealed flow communication with the passages 63 and 65, respectively. As shown in FIG. 2, the assembly 19 is secured to the nozzle 69 by a keeper nut 77 which, when tightened, urges the assembly 19 into sealing contact with the nozzle 69.

Such construction makes replacement of a broken needle assembly 19 extremely easy and quick. One need only remove the receptacle guide 23 (as described below), unscrew the keeper nut 77, remove and replace the assembly 19 and replace the keeper nut 77 and the receptacle guide 23.

Figure 11:
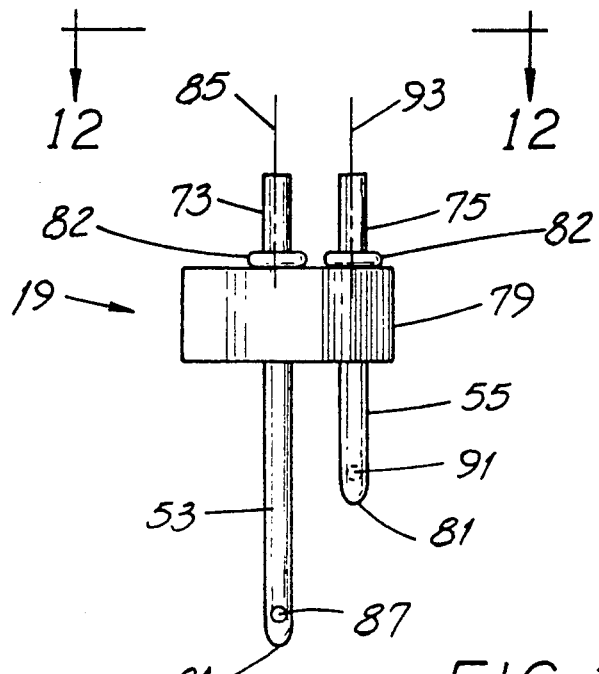
FIG. 11 is a side elevation view, with part in dashed outline, of the needle assembly component of the assembly of FIG. 1.
Figure 12:
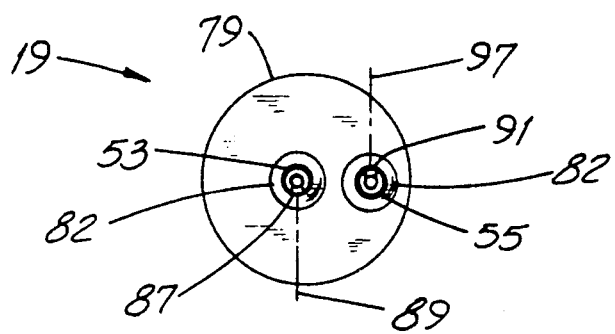
FIG. 12 is a top plan view of the needle assembly component of FIG. 11 taken along the viewing plane 12—12 thereof.

Referring particularly to FIGS. 11 and 12, the needle assembly 19 has a disc-like body 79 through which the needles 53,55 extend, both above and below. Above the body 79, each needle 53, 55 terminates in an aforementioned ferrule 73, 75 sized to fit snugly into the appropriate nozzle passage. Each ferrule 73, 75 is fitted with an O-ring seal 82 and the lower ends of the passages 63, 65 are appropriately machined to receive such seals 82.

Those portions of the needles 53, 55 extending below the body 79 are of differing lengths, the longer sampling needle 53 for directing the specimen sample from the process lines 29, 31 into the receptacle 25 and the shorter venting needle 55 for providing a "reverse direction" flow path for displaced air to be expelled from the specimen receptacle 25 as such receptacle fills with liquid.

At least one needle 53, 55 (and preferably each needle 53, 55) has a rounded or blunt end 81 whereby septum coring is substantially prevented. This feature is better appreciated when contrasted with conventional "hypodermic-like" needles having a sharp tip and a bevelled face which often cut a neat, disc-like core out of the septum 83. Volatile fluids thereby undesirably escape from the receptacle 25. Examples of such sharp needles are shown in the Carpenter et al. patent and the Tech-Quip, Inc. literature discussed above.

And there are yet other innovative features in the new valve assembly 10. In another aspect of the invention, the sampling needle 53 includes a long axis 85 extending toward the bottom of the bottle-like receptacle 25. A fill port 87 (the small opening from which a liquid flows from the needle 53 into the receptacle 25) extends along a port axis 89 generally normal to the long axis 85 of the needle 53. This "side-porting" arrangement substantially avoids liquid frothing which may occur with prior art needles which are "downported" and flow incoming fluid directly into the surface of the liquid already in the receptacle 25.

In a highly preferred embodiment, the venting needle 55 includes a vent port 91 and the fill port 87 and the vent port 91 are directed generally away from one another. This helps avoid fluid "carryover" which may occur if fluid expelled from the fill port 87 is directed toward the vent port 91 of the venting needle 55.

Furthermore, the venting needle 55 also includes a long axis 93 extending toward the receptacle bottom 95. The vent port 91 is similarly along an axis 97 generally normal to the long axis 93 of the venting needle 55 and, in use, is displaced vertically from the fill port 87 to further aid in avoiding fluid carryover.

Figure 13:
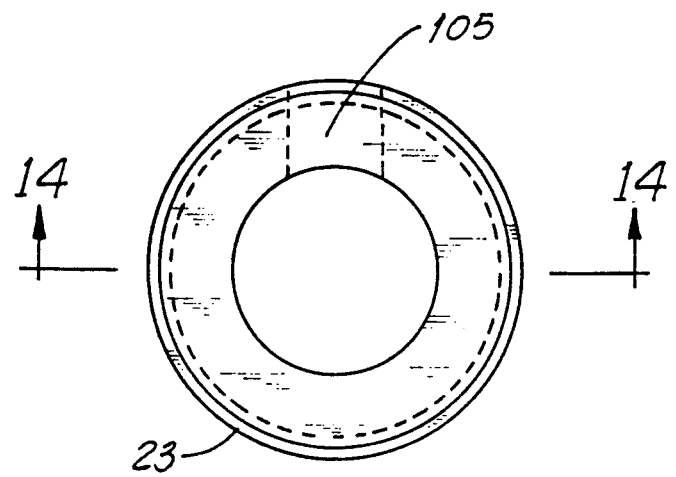
FIG. 13 is a top plan view of the receptacle guide component of the assembly of FIG. 1.
Figure 14:
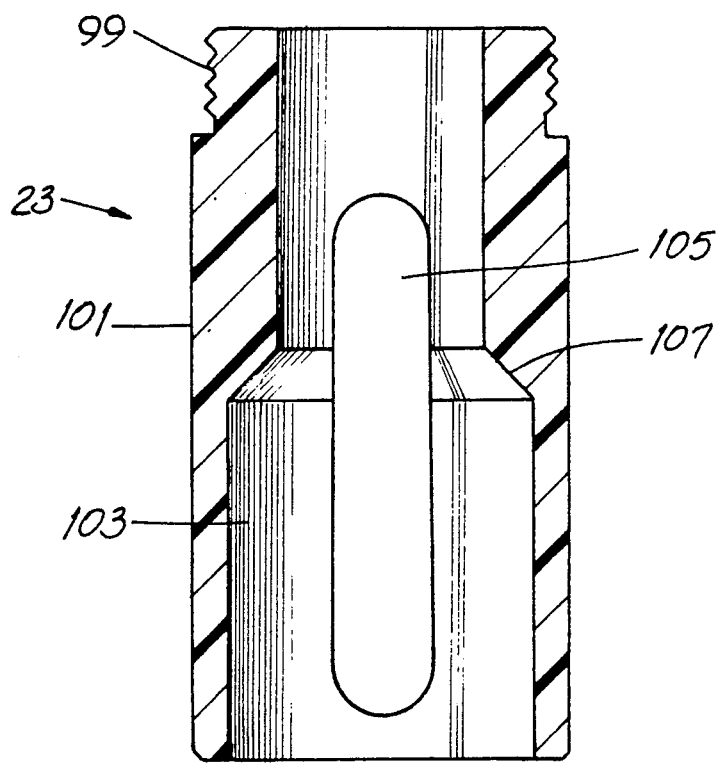
FIG. 14 is a cross section view of the receptacle guide component of FIG. 13 taken along the viewing plane 14—14 thereof.

And there are yet other features which help make the new valve assembly 10 very convenient to use. Referring also to FIGS. 2, 13 and 14, the assembly 10 has a lower end with a threaded receptacle guide attachment ring 21 mounted thereon. The threaded upper end 99 of the receptacle guide 23 is urged toward the ring 21 while the latter is rotated to engage the end 99 and secure the guide 23 to the assembly 10.

The receptacle guide 23 has a generally cylindrical exterior surface 101 and an interior cavity 103 generally conforming to the shape and dimensions of the receptacle 25. When the receptacle 25 is inserted into the guide 23 with slight sliding clearance therebetween, the receptacle 25 is guided for aligned engagement of the septum 83 with the needle assembly 19 until the receptacle 25 contacts the guide shoulder 107.

The receptacle guide 23 also includes an elongate viewing aperture 105 permitting visual inspection of the receptacle contents and, more particularly, of the level of liquid 80 in the receptacle. In one preferred embodiment, the guide 23 is formed of molded nylon plastic material. However, it is to be appreciated that other materials and other interior cavity shapes may be selected depending upon the nature of the liquid 80 being sampled and depending upon the shape of the receptacle 25. Such variations are, of course, contemplated by the invention.

In use, the lines 29 and 31 of the sampling valve assembly 10 are connected in series with a line carrying the liquid 80 to be periodically sampled. The handle 35 of the diverting valve 11 is initially positioned so that no liquid 80 is permitted to flow to the passage 47. When a sample is to be taken, a septum-closed receptacle 25 is inserted into the guide 23 until both needles 53, 55 have pierced the septum 83 and the cap of the receptacle 25 is seated against the keeper nut 77.

The isolation valve 15 is opened slightly and the diverting valve 11 is then "cracked" slightly open to the passage 47 to supply liquid 80 through the pressure-reducing orifice passage 43 to the isolation valve 15. So positioned, the diverting valve 11 acts as a pressure reducing valve, the effective cross-sectional area of which can be changed by manipulating the handle 35.

The isolation valve 15 is then opened to the degree necessary to obtain a reasonable flow rate of liquid 80 into the receptacle 25. And of course, the maximum flow rate can be set by adjustable stops at the isolation valve 15 and/or the diverting valve 11 to allow either or both valves 11, 15 to function as a pressure reducing valve. After taking the sample, the isolation valve 15 is closed and the diverting valve 11 is returned to the non-sampling position.

Because of the radial port 87 in the sampling needle 53, the flowing liquid 80 is directed toward the rear of the receptacle 25 (away from the user) rather than toward the bottom 95. As described above, the benefits include avoidance of frothing of any earlier-drawn liquid 80, better sight gauging and directing of liquid 80 away from the user in the event of receptacle breakage or user error.

When the receptacle 25 is filled with the desired quantity of the liquid 80 (to a level below the ends of the needles 53, 55 as determined by looking through the viewing aperture 105), the valves 11, 15 are shut off. If the optional purge feature is used, the system is purged with the receptacle 25 fully seated, with valve 11 off and with valve 15 open.

In the illustrated embodiment, the handle 35 of the diverting valve 11 (which has a 180° "throw") is down to permit liquid 80 to flow along the lines 29, 31 but not to the orifice passage 43. When the handle 35 is up or at some intermediate position, liquid 80 is permitted to flow to the orifice passage 43. The handle 59 of the isolation valve 15 (which has a 90° "throw") is horizontal when closed and downward when fully open to flow liquid 80 to the receptacle 25. Of course, other handle arrangements can be used, with or without adjustable stops as mentioned above.

While the principles of the inventive assembly 10 have been shown and described in connection with only a few embodiments, it is to be clearly understood that such embodiments are by way of example only.

We claim:

1. In a valve assembly for supplying a fluid specimen and having a body, an input flow line attached to the body, an output flow line attached to the body and a body-mounted process valve with an inlet port receiving fluid from the input flow line and a sampling line directing the fluid to a receptacle having a septum, the improvement comprising:

a pressure-reducing orifice plate mounted to the body;

a needle assembly having a sampling needle and a venting needle separate from the sampling needle; and, an isolation valve mounted to the body and providing redundant shutoff;

and wherein:

the process valve, the orifice plate and the isolation valve are in series flow communication with one another;

each needle has a blunt end for preventing septum coring; and, at least one of the needles has a side port, thereby substantially preventing fluid carryover.

2. The assembly of claim 1 wherein the orifice plate is between the process valve and the isolation valve.

3. The assembly of claim 1 wherein the isolation valve includes a round valving member rotatably adjustable in a continuum between a fully closed position and a fully open position, thereby permitting metered fluid flow to the receptacle.

4. The assembly of claim 3 wherein the process valve includes a round valving member rotatably adjustable in a continuum between a first position, an intermediate position and a second position and wherein:

in the intermediate position, the valving member connects the inlet port to the output flow line and to the isolation valve; and, in the second position, the valving member connects the inlet port only to the isolation valve.

5. The assembly of claim 3 wherein the process valve includes a round valving member rotatably adjustable between a first position connecting the inlet port only to the output flow line and a second position connecting the inlet port only to the isolation valve.

6. The assembly of claim 1 further including
a vent port;
a passage extending from the sampling line to the vent port; and,
a purge passage for flowing purging gas through the assembly, the purge passage being in flow communication between a source of purging gas and the sampling line and the vent port for purging the passage extending from the sampling line to the vent port,
whereby substantially all residual fluid may be purged from the assembly.

7. The assembly of claim 6 wherein the orifice plate is adjacent to the process valve.

8. The valve assembly of claim 1 wherein:
each needle has blunt end.

9. The valve assembly of claim 8 wherein the receptacle has a bottom, the valve assembly contains a liquid fluid to be sampled, the side port is in the sampling needle and the sampling needle further includes:
a sampling needle axis coextensive with the sampling needle and extending toward the bottom; and,
the sampling needle side port is along a port axis substantially normal to the sampling needle axis,
whereby liquid frothing is substantially avoided.

10. The valve assembly of claim 8 wherein the receptacle has a bottom and:
the sampling needle side port is along a sampling needle side port axis substantially parallel to the bottom;
the venting needling includes a vent port along a venting needle vent port axis substantially parallel to the bottom; and,
the the port axes define an angle of at least 45° therebetween,
whereby fluid carryover is substantially avoided.

11. The valve assembly of claim 8 further including:
a nozzle connected to the isolation valve;
the needle assembly is attached to the nozzle;
and wherein the needle assembly is detachable from the nozzle as a unitary structure.

12. The valve assembly of claim 11 wherein the needle assembly is retained by a keeper nut limiting travel of the receptacle to a location where the needles have pierced the septum.

13. The valve assembly of claim 12 wherein the needle assembly is retained solely by the keeper nut.

14. The assembly of claim 1 wherein the receptacle has a tapered neck, the assembly includes (a) a needle assembly attached thereto, (b) a lower end and (c) a receptacle guide attached to the lower end and wherein:
the receptacle guide has a tapered guide shoulder substantially conforming to the shape of the tapered neck,
whereby the septum is brought to aligned engagement with the needle assembly.

15. The assembly of claim 14 wherein:
the receptacle guide is substantially cylindrical and of one-piece construction; and,
the cavity has a substantially cylindrical portion and a tapered neck portion.

16. The assembly of claim 14 wherein:
the receptacle guide includes an elongate aperture permitting viewing of the receptacle contents.

17. In a valve assembly for supplying a fluid specimen and having an input flow line, an output flow line and a process valve with an inlet port receiving fluid from the input flow line and a sampling port directing the fluid to a receptacle, the improvement comprising:
an isolation valve connected between the sampling port and the receptacle for providing redundant shutoff, the isolation valve being in series with the process valve and the receptacle and including a round valving member rotatably adjustable in a continuum between a fully closed position and a fully open position;
and wherein:
the process valve includes an outlet port in flow communication with the sampling port and permitting fluid flow from the input flow line to the sampling port and the outlet port, the process valve including a round valving member rotatably adjustable in a continuum between a first position, and intermediate position and a second position and wherein:
in the first position, the valving member connects the inlet port only to the output flow line;
in the intermediate position, the valving member connects the inlet port to the output flow line and to the isolation valve; and,
in the second position, the valving member connects the inlet port only to the isolation valve.

18. In a valve assembly for supplying a fluid specimen and having an input flow line, an output flow line and a process valve with an inlet port receiving fluid from the input flow line and a sampling port directing the fluid to a receptacle, the improvement comprising:
an isolation valve connected between the sampling port and the receptacle for providing redundant shutoff;
the process valve includes an outlet port in flow communication with the sampling port and permitting fluid flow from the input flow line to the sampling port and the outlet port;
and the assembly further includes:
a vent port;
a flow passage extending from the sampling line to the vent port; and,
a purge passage for flowing purging gas through the assembly, the purge passage being in flow communication between a source of purging gas and the sampling line and the vent port for purging the passage extending from the sampling line to the vent port,
whereby substantially all residual fluid may be purged from the assembly.

19. The assembly of claim 18 wherein the flow passage includes a pressure reducing orifice connected between the process valve and the isolation valve.

* * * * *